US009205229B2

(12) United States Patent
Khalaj

(10) Patent No.: US 9,205,229 B2
(45) Date of Patent: Dec. 8, 2015

(54) CATHETER ADVANCEMENT DEVICE

(71) Applicant: Kimberly-Clark Worldwide, Inc., Neenah, WI (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 148 days.

(21) Appl. No.: 14/061,825

(22) Filed: Oct. 24, 2013

(65) Prior Publication Data

US 2015/0119860 A1 Apr. 30, 2015

(51) Int. Cl.
*A61M 25/01* (2006.01)
*A61M 25/09* (2006.01)

(52) U.S. Cl.
CPC ..... *A61M 25/0113* (2013.01); *A61M 25/09041* (2013.01)

(58) Field of Classification Search
CPC ................... A61M 25/0113; A61M 25/09041
USPC ......................................... 604/159, 161, 528
See application file for complete search history.

(56) References Cited

U.S. PATENT DOCUMENTS

| 3,774,605 | A | | 11/1973 | Jewett |
| 3,835,854 | A | | 9/1974 | Jewett |
| 5,235,987 | A | | 8/1993 | Wolfe |
| 5,346,498 | A | * | 9/1994 | Greelis et al. ................. 606/108 |
| 5,882,294 | A | | 3/1999 | Storz et al. |
| 8,430,889 | B2 | | 4/2013 | Zeng et al. |
| 2004/0082880 | A1 | | 4/2004 | Heh et al. |
| 2005/0171568 | A1 | | 8/2005 | Duffy |
| 2006/0229587 | A1 | * | 10/2006 | Beyar et al. ................... 604/510 |
| 2010/0041990 | A1 | | 2/2010 | Schlitt et al. |
| 2010/0312227 | A1 | | 12/2010 | House |

FOREIGN PATENT DOCUMENTS

| WO | WO 2011/143621 A1 | 11/2011 |
| WO | WO 2012/159000 A2 | 11/2012 |
| WO | WO 2013/019806 A2 | 2/2013 |

OTHER PUBLICATIONS

PCT Search Report, Feb. 5, 2015.

* cited by examiner

*Primary Examiner* — Imani Hayman
(74) *Attorney, Agent, or Firm* — Dority & Manning, P.A.

(57) ABSTRACT

A catheter advancement device includes a housing with a catheter inlet, a catheter outlet, and a manually actuated finger drive mechanism. The drive mechanism frictionally engages a catheter inserted into the inlet and advances the catheter through the housing and into or out of another device, such as a needle. The housing may be slidable along the needle.

10 Claims, 3 Drawing Sheets

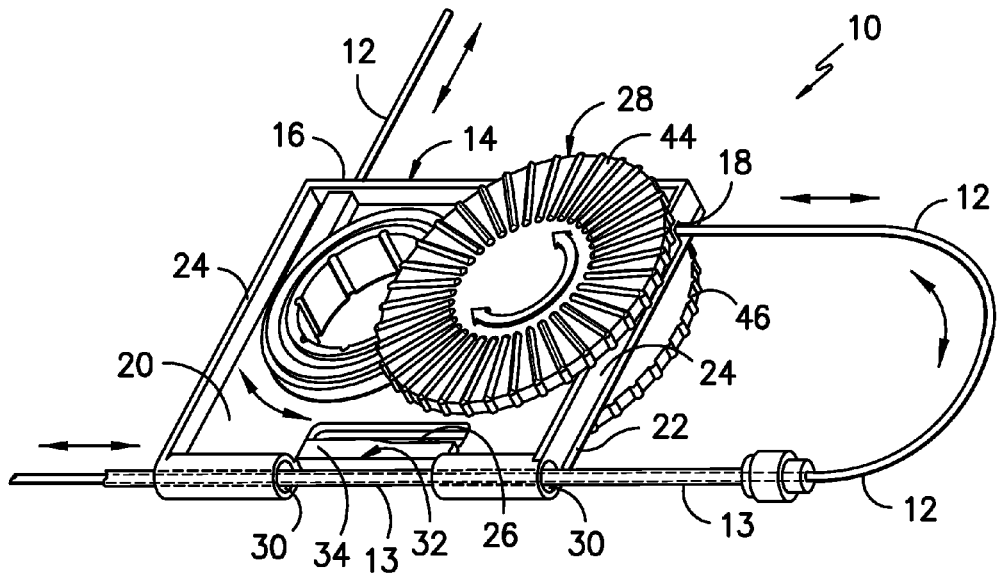
FIG. -1-
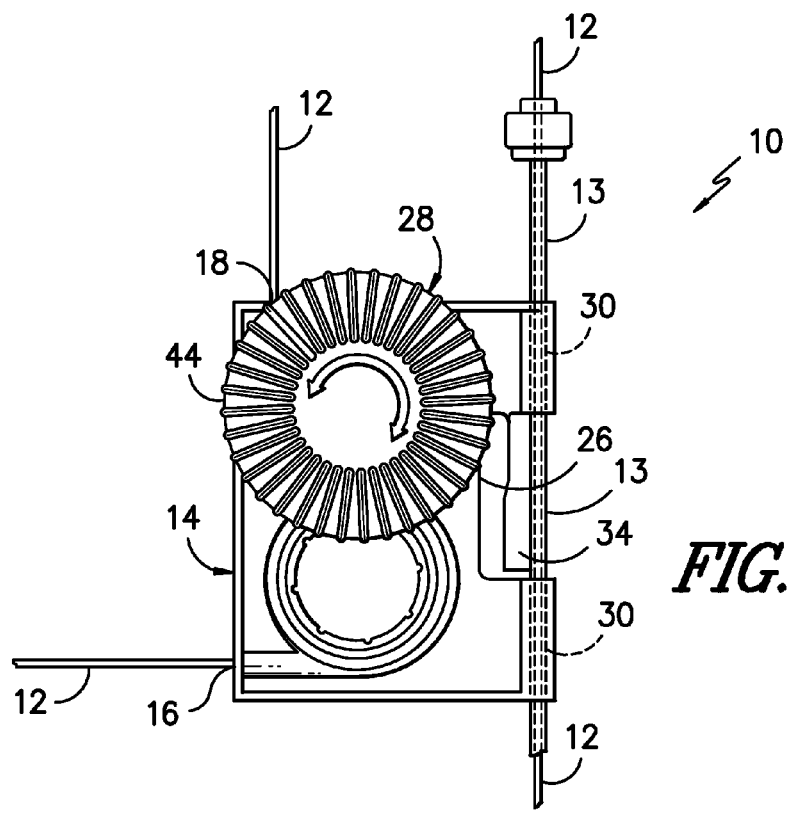
FIG. -2-

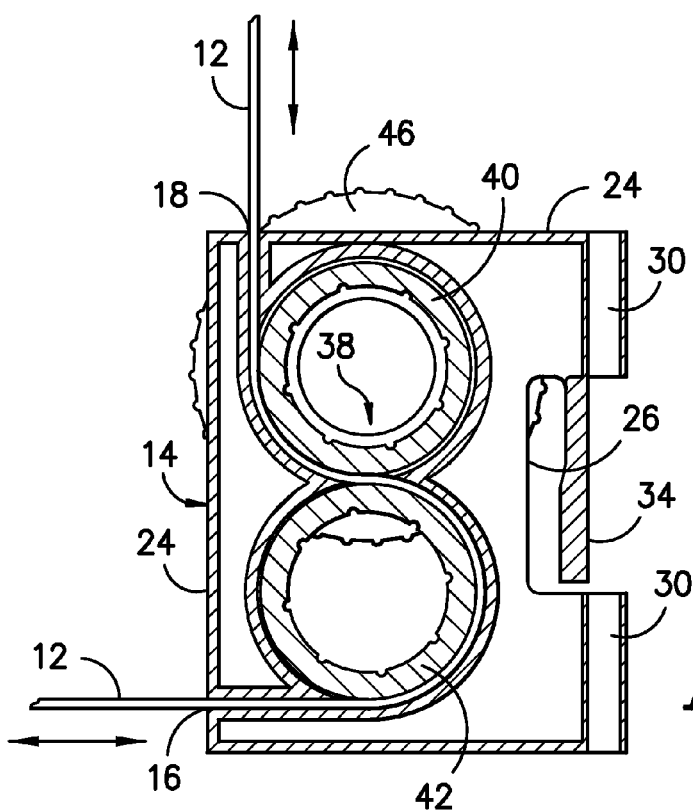
FIG. -3-
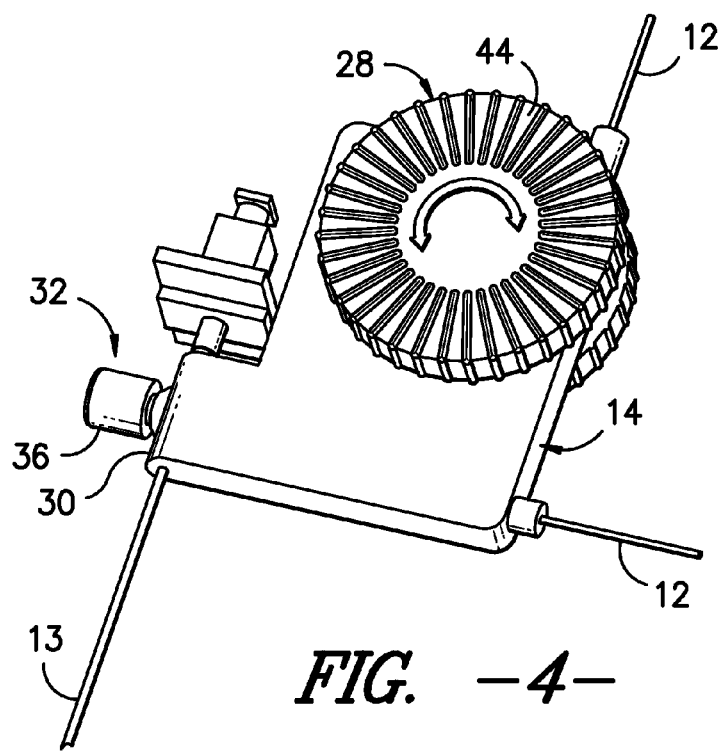
FIG. -4-

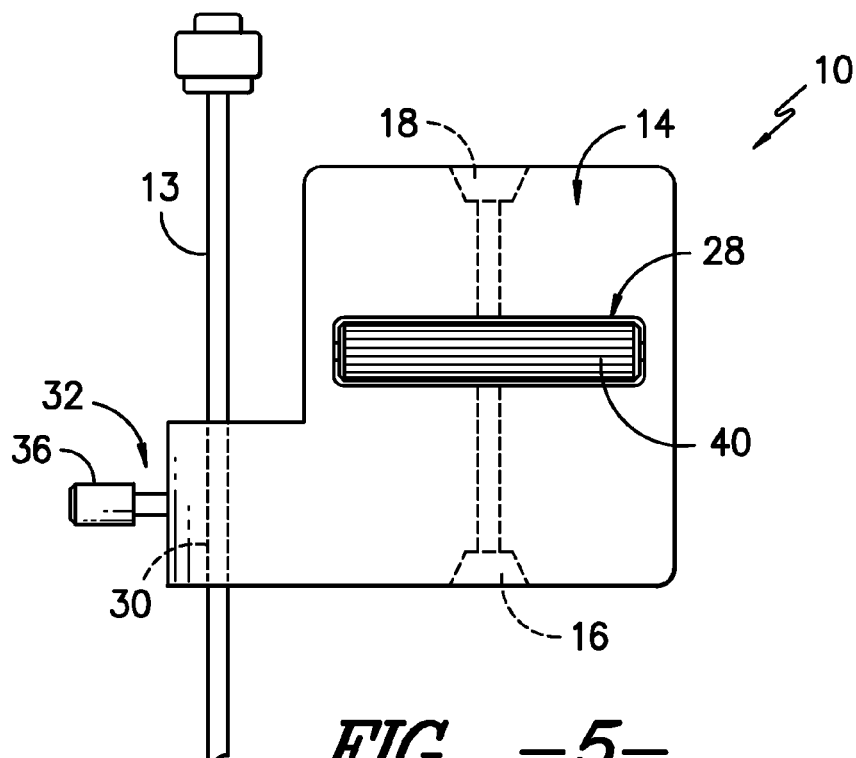
FIG. -5-
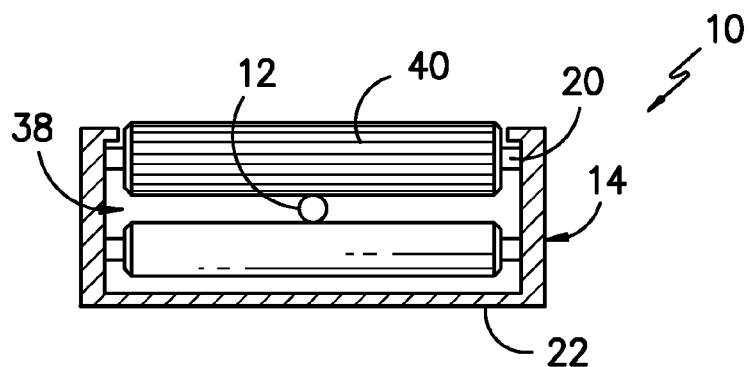
FIG. -6-
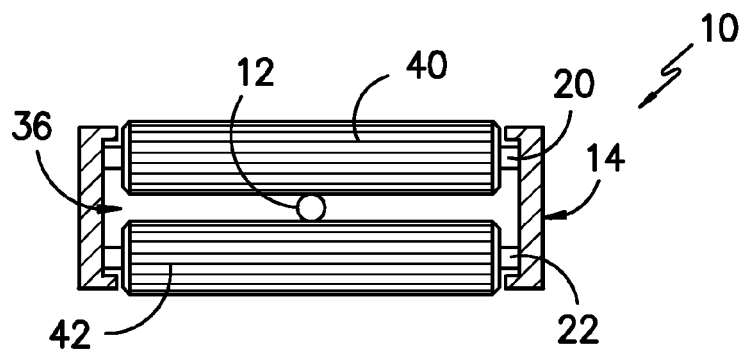
FIG. -7-

CATHETER ADVANCEMENT DEVICE

FIELD OF THE INVENTION

The present invention relates generally to the field of medical catheters, and more particularly to a device for advancing a catheter through a needle or other tubular device into a patient.

BACKGROUND

Ultrasound imaging for needle placement in various medical procedures is well known, particularly for peripheral nerve blocks wherein a drug is delivered to a target site within a patient via a catheter. With such procedures, an ultrasound probe is used to identify the target region and to provide an image of needle advancement to the target region. Once location of the needle tip within the target region is verified, the drug may be delivered through the needle. In certain procedures where long-term or continuous drug delivery is needed, the physician advances an infusion catheter through the needle so that the tip of the catheter is also placed in the target region. The needle may then be removed and drug delivery commenced through the catheter.

A drawback associated with the conventional ultrasound imaging system and procedure is that the physician generally uses one hand to hold and manipulate the ultrasound probe against the patient, while the other hand is used to guide the needle to the identified target region. Once the needle tip has been placed and verified within the target region, the physician must hold the needle as steady as possible. A separate assistant must then use a delivery device (e.g., a syringe) to inject the drug through the needle, or to thread a catheter through the needle, while the physician holds the needle steady and controls the ultrasound probe. This procedure is tedious, cumbersome, and requires multiple persons.

Devices have been suggested to aid the physician by locking or immobilizing the needle relative to the ultrasound probe. Reference is made, for example, to U.S. Patent Application Publication 2010/0041990 published on Feb. 18, 2010; Patent Application Publication 2010/0312121 published on Dec. 9, 2010; and International Publication No. WO 2013/019806 published on Feb. 7, 2013. These devices, however, may be problematic in certain procedures in that they do not allow for independent control and manipulation of the needle remote from location of the ultrasound probe.

A device that allows the physician to hold an introducer needle remote from the ultrasound probe and steady within a target region while simultaneously advancing a catheter through the needle with a single hand would be desirable. The present invention provides such a device.

SUMMARY OF THE INVENTION

Objects and advantages of the invention will be set forth in part in the following description, or may be obvious from the description, or may be learned through practice of the invention.

In certain aspects, the present invention relates to a unique catheter advancement device that is particularly useful in nerve block procedures. The device includes a housing having a catheter inlet and a catheter outlet, wherein a catheter, such as an infusion catheter, is threaded into the inlet, through the housing, and out of the outlet. A manually actuated finger drive mechanism is configured intermediate of the catheter inlet and the catheter outlet. This drive mechanism frictionally engages the catheter inserted through the housing and allows a clinician to advance the catheter in either direction through the housing by manipulating the drive mechanism with a single finger (which may be the clinician's thumb).

In a particularly useful embodiment, the housing further includes a needle channel configured for insertion of a needle, e.g., an introducer needle, therethrough, and a lock mechanism. The housing is slidable along the needle after the needle is inserted through the channel and the housing can be locked in a fixed relative position on the needle by the lock mechanism. With this configuration, the clinician may position the device at a fixed location on the introducer needle and use a single hand to manipulate and hold the needle steady while simultaneously advancing the catheter through the needle with the same hand.

It should be understood that the channel may be defined at any suitable location on the housing depending on the shape and size of the housing. In a particular embodiment, the needle channel is defined by pipe-like structure along an edge of the housing.

The lock mechanism may be any suitable mechanical or frictional retarding lock that serves to secure the housing at a fixed location along the needle, at least to the extent to prevent inadvertent or unintended slippage of the housing relative to the needle. For example, the lock may be a simple set screw that engages against the needle when tightened. In a particular embodiment, the lock mechanism includes a biased arm or lever that extends into the channel to frictionally engage the needle with sufficient force to prevent unintended slippage of the housing relative to the needle.

The finger drive mechanism may be variously configured. In particular embodiments, the drive mechanism is a nip drive, wherein the catheter passes through the nip defined between a drive wheel and an opposed surface, such as an idler wheel or other bearing surface, with the drive wheel being a finger actuated drive wheel. For example, in a certain embodiment, the housing may include a front panel member and an opposed back panel member, with the front and back panel members extending is parallel planes. The nip drive includes a drive wheel and an idler wheel disposed between the front and back panel members, with the wheels disposed in a common plane and having a rotational axis that is perpendicular to the front and back panel members. This configuration provides a slim, compact, and efficient design that is easily manipulated and controlled by the clinician.

The drive may also include a first external finger plate attached to the drive wheel, wherein the finger plate extends outwardly from one of the front or back panel members for external manual manipulation of the drive wheel. In a further embodiment, a second external finger plate is attached to the drive wheel on a side of the housing opposite to the first external finger plate such that the housing is essentially sandwiched between the finger plates. The drive wheel can be controlled from either side of the housing in this embodiment. It may be further advantageous for one or both of the finger plates to extend radially beyond an edge of the housing so that the clinician also has the option to control the drive wheel by moving a finger along the edge of the housing.

In yet another embodiment, the drive wheel and an idler wheel may be disposed at least partially within the parallel front and back panel members with a respective rotational axis that is parallel to said front and back members. A circumferential portion of the drive wheel extends outwardly through one of the front or back panel members for manual manipulation of the drive wheel. A circumferential portion of each of the drive wheel and idler wheel may extend outwardly through a respective one of the front or back members, wherein the drive wheel and idler wheel are thus functionally interchangeable (e.g., either wheel may be a drive wheel while the other wheel is the idler wheel).

The catheter advancement device in accordance with the present invention provides numerous advantages. For example, the device allows the clinician to place the device over a needle, such as an introducer needle, before inserting the needle into the patient and, with the needle in the body, the clinician can advance the catheter to the target location without moving the needle. The device also aids the clinician in certain procedures, such as creating a fluid pool at a target location, by attaching the device to the proximal end of the catheter (without necessarily sliding the device onto a needle) and using the device for more controlled catheter advancement.

Aspects of the invention will be described in greater detail below with reference to specific embodiments depicted in the figures.

BRIEF DESCRIPTION OF THE DRAWINGS

FIG. 1 is a perspective view of an exemplary catheter advancement device in accordance with aspects of the invention;

FIG. 2 is a top view of the device of FIG. 1;

FIG. 3 is a top view of the device of FIG. 1 with the top panel member removed;

FIG. 4 is a perspective view of an alternative embodiment of a catheter advancement device in accordance with aspects of the invention;

FIG. 5 is a top view of another embodiment of a catheter advancement device;

FIG. 6 is a cross-sectional view of the device of FIG. 5 taken along the lines indicated in FIGS. 6; and FIG. 7 is a cross-sectional view of an alternative nip drive that may be used in a device in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the device is the end oriented towards a catheter insertion site), and "proximal" refers to the opposite direction (e.g., a catheter is inserted into the proximal end of the device).

Referring to FIG. 1, an embodiment of a catheter advancement device 10 in accordance with aspects of the invention is depicted. The device 10 includes a housing 14 that may have any design shape, size, or configuration, and may include any number of independent housing components. The rectangular shape of the housing 14 with multiple edges 24 in FIG. 1 is for illustrative purposes only.

The housing 14 includes a catheter inlet 16 and a catheter outlet 18, wherein a catheter 12, such as an infusion catheter used in a nerve block procedure, is directed into the inlet 16, threads through the housing 14, and exits out of the outlet 18.

From the outlet 18, the catheter 12 is inserted into the proximal end of a needle 13, as illustrated in FIG. 1.

The device 10 includes a manually actuated finger drive mechanism 28. For the embodiments shown in FIGS. 1 through 7, the finger drive mechanism 28 is operably configured intermediate of the catheter inlet 16 and the catheter outlet 18. This drive mechanism 28 frictionally engages the catheter 12 inserted through the housing 14 and allows a clinician to advance the catheter 26 in either direction through the housing 14 by manipulating the drive mechanism 28 with a single finger (which may be the clinician's thumb). Embodiments of the drive mechanism 28 are described in greater detail below.

The housing 14 further includes a channel 30 configured for insertion of the needle 13 therethrough. In the illustrated embodiment of FIG. 1, this channel 30 is defined by axially spaced tunnel-like members configured along an edge 24 and separated by an edge recess 26. In other embodiments, the needle channel 30 may be defined by a single structure, such as the configurations of FIGS. 4 and 5. It should be understood that the term "channel" is used herein to encompass any type of structure that receives and accommodates sliding movement of the needle 13 relative to the housing 14.

The device 10 may also include any suitable type of lock mechanism 32 operably configured with the housing 14 to fix the housing at a desired position relative to the needle 14. This ability may be needed in certain medical procedures wherein the length of the needle inserted into the patient depends on any number of factors, such as patient physiology, target site, and for forth. With the housing 14 fixed in position on the needle 13 via the lock mechanism 32, the clinician may position the device 10 at a fixed location on the introducer needle 13 and use a single hand to manipulate and hold the needle 13 steady while simultaneously advancing the catheter 12 through the needle 13 with the same hand.

The lock mechanism 32 may be any suitable mechanical locking or frictional retarding mechanism that serves to secure the housing 14 at a fixed location along the needle 13. In the embodiment depicted in FIGS. 4 and 5, the lock mechanism 32 is defined by a set screw 36 that engages against the needle 13 when tightened. In an alternate embodiment depicted in FIGS. 1 through 3, the lock mechanism is defined by a biased lever or arm 34 positioned within a recess 26 between components of the channel 30. This arm is biased at least partially into the passageway defined by the channel 30 so as to frictionally engage against the needle 13 inserted through the components 30. The arm 34 generates sufficient frictional resistance to prevent unintended slippage of the housing 14 relative to the needle 13. This particular embodiment presents a passive lock mechanism in that the clinician need not activate or set the lock. The lock mechanism is always engaged by the frictional resistance between the needle 13 and the arm 34.

The finger drive mechanism 28 may be variously configured. In the particular embodiments illustrated in FIG. 3, the drive mechanism 28 is a nip drive 38, wherein the catheter 12 passes through a nip defined between a drive wheel 40 and an opposed bearing surface, which may be a stationary surface. In the depicted embodiment, the bearing surface is a freely rotatable idler wheel 42. The drive wheel 40 and idler wheel 42 are rotatably mounted within the housing 14 by any suitable bearing arrangement. The drive wheel 40 is the member that is manually actuated by the clinician's finger(s) directly or via another member.

In the embodiments of FIGS. 1 through 3, the housing 14 may include a front member 20 and an opposed back member 22, wherein the front and back members may be panel-like members extending is parallel planes. The nip drive 38 includes the drive wheel 40 and idler wheel 42 disposed between the front and back panel members 20, 22, with the wheels 40, 42 disposed in a common plane and having a rotational axis that is perpendicular to the front and back members 20, 22. This configuration of the device 10 provides a slim, compact, and efficient design that is easily manipulated and controlled by the clinician.

The nip drive 38 may also include a first external finger plate 44 attached to the drive wheel 40 through the front panel member 20. In this manner, the finger plate 44 extends outwardly from one of the panel members for easy external access and manual manipulation of the drive wheel 40. In a further embodiment depicted in FIGS. 1, 3, and 4, a second external finger plate 46 is attached to the drive wheel on a side of the housing 14 opposite to the first external finger plate 44 such that the housing 14 is essentially sandwiched between the finger plates 44, 46. With this configuration, the drive wheel 40 can be controlled by the clinician from either side of the housing 14. As depicted in the figures, it may be advantageous for one or both of the finger plates 44, 46 to extend radially beyond an edge 24 of the housing 14 so that the clinician also has the option to control the drive wheel 40 by moving a finger along the housing edge 24.

FIGS. 5 through 7 depict an alternative embodiment wherein the drive wheel 40 and an idler wheel 42 may be disposed at least partially within the parallel front and back panel members 20, 22 with a respective rotational axis that is parallel to the front and back members. As can be readily appreciated from FIGS. 5 and 6, a circumferential portion of the drive wheel 40 extends outwardly through one of the front or back panel members 20, 22 for manual manipulation of the drive wheel by a clinician simply sliding their finger along the respective panel member to engage the drive wheel 40. In the embodiment of FIG. 6, the idler wheel is completely housed within the housing 14 and the drive wheel 40 is exposed through the panel member 20. In an alternate embodiment depicted for example in FIG. 7, a circumferential portion of the drive wheel 40 and of the idler wheel 42 extends outwardly through a respective one of the front or back members 20, 22. In this embodiment, the drive wheel 40 and idler wheel 42 are thus functionally interchangeable (e.g., either wheel may be a drive wheel while the other wheel is the idler wheel).

It should be appreciated that the device 10 may be utilized in certain procedures without attaching the device to a needle. For example, the device 10 may simply be used as a means for more controlled advancement of a catheter into and out of a patient, for example when creating a fluid pool at a target location by injecting fluid through the catheter as the catheter is advanced or retracted, without necessarily attaching the device 10 to a needle.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A catheter advancement device, comprising:
a housing, said housing including a catheter inlet and a catheter outlet;
a manually actuated finger drive mechanism intermediate of said catheter inlet and said catheter outlet; wherein said drive mechanism frictionally engages a catheter inserted into said housing and advances the catheter through said housing; wherein said drive mechanism comprises a nip drive, said nip drive having a finger actuated drive wheel;
wherein said housing further comprises a channel and a lock mechanism, wherein said housing is slidably positionable along a needle inserted through said channel and lockable in a fixed relative position on the needle by said lock mechanism; wherein said lock mechanism comprises a biased arm positioned along said channel so as to frictionally engage against and fix the position of the needle relative to the housing.

2. The catheter advancement device as in claim 1, wherein said channel is configured along an edge of said housing.

3. The catheter advancement device as in claim 1, wherein said nip drive further comprises an idler wheel opposed to said drive wheel.

4. The catheter advancement device as in claim 3, wherein said housing comprises a front member and an opposed back member, said front and back members extending in parallel planes, said drive wheel and said idler wheel disposed between said front and back members with a rotational axis that is perpendicular to said front and back members.

5. The catheter advancement device as in claim 4, further comprising a first external finger plate attached to said drive wheel for manual manipulation of said drive wheel.

6. The catheter advancement device as in claim 5, further comprising a second external finger plate attached to said drive wheel on a side of said housing opposite to said first external finger plate.

7. The catheter advancement device as in claim 6, wherein at least one of said first or second external finger plates extends radially beyond an edge of said housing.

8. The catheter advancement device as in claim 3, wherein said housing comprises a front member and an opposed back member, said front and back members extending in parallel planes, said drive wheel and said idler wheel disposed at least partially between said front and back members with a rotational axis that is parallel to said front and back members.

9. The catheter advancement device as in claim 8, wherein a circumferential portion of said drive wheel extends outwardly through one of said front or back members for manual manipulation of said drive wheel.

10. The catheter advancement device as in claim 8, wherein a circumferential portion of each of said drive wheel and said idler wheel extends outwardly through a respective one of said front or back members, wherein said drive wheel and said idler wheels are functionally interchangeable.

* * * * *